(12) United States Patent
Hu et al.

(10) Patent No.: US 11,369,423 B2
(45) Date of Patent: Jun. 28, 2022

(54) MEDICAL ANTI-LOOSENING SCREW BASED ON ORGANISM OSTEOGENESIS FUNCTION

(71) Applicants: Siwang Hu, Zhejiang (CN); Jianru Xiao, Shanghai (CN)

(72) Inventors: Siwang Hu, Zhejiang (CN); Jianru Xiao, Shanghai (CN); Xiaopan Cai, Shanghai (CN); Hong Ding, Shanghai (CN); Shungui Chen, Shanghai (CN); Tielong Liu, Shanghai (CN)

(73) Assignee: Siwang Hu, Shanghai (CN)

( * ) Notice: Subject to any disclaimer, the term of this patent is extended or adjusted under 35 U.S.C. 154(b) by 0 days.

(21) Appl. No.: 16/645,412

(22) PCT Filed: Apr. 16, 2019

(86) PCT No.: PCT/CN2019/082922
§ 371 (c)(1),
(2) Date: Mar. 6, 2020

(87) PCT Pub. No.: WO2019/210774
PCT Pub. Date: Nov. 7, 2019

(65) Prior Publication Data
US 2021/0106370 A1 Apr. 15, 2021

(30) Foreign Application Priority Data

May 4, 2018 (CN) .......................... 201820664990.2

(51) Int. Cl.
*A61B 17/86* (2006.01)
(52) U.S. Cl.
CPC ...... *A61B 17/8625* (2013.01); *A61B 17/8605* (2013.01); *A61B 2017/8655* (2013.01)

(58) Field of Classification Search
CPC ......... A61B 17/8625; A61B 2017/8655; F16B 35/041; F16B 25/0078
(Continued)

(56) References Cited

U.S. PATENT DOCUMENTS 4,486,135 A * 12/1984 Kazino ............... F16B 25/0021
411/416
8,348,573 B2 * 1/2013 Chang ................. F16B 25/0078
411/387.1
(Continued)

FOREIGN PATENT DOCUMENTS

CN 201034104 Y 3/2008
CN 205019148 U 2/2016
(Continued)

OTHER PUBLICATIONS

IB; International Search Report dated Jun. 25, 2019 in Application No. PCT/CN2019/082922.
(Continued)

*Primary Examiner* — Kevin T Truong
*Assistant Examiner* — Tracy L Kamikawa
(74) *Attorney, Agent, or Firm* — Snell & Wilmer L.L.P.

(57) ABSTRACT

The present application relates to the technical field of medical instruments and provides an anti-loosening medical screw based on an organism osteogenesis function. The medical anti-loosening screw comprises a screw cap and a screw rod connected to the screw cap. The screw rod comprises a main rod and a thread spirally wound around the main rod. The cross section of the main rod is non-circular. The present medical anti-loosening screw based on an organism osteogenesis function can be applied to the medical fields such as orthopedics (spine, four limbs, pelvis, joints, etc.), maxillofacial surgery, odontology, and veteri-
(Continued)

narians and can be effectively prevented from loosening after operation after being implanted.

9 Claims, 3 Drawing Sheets

(58) Field of Classification Search
USPC .................................................. 411/416, 424
See application file for complete search history.

(56) References Cited

U.S. PATENT DOCUMENTS

| | | | |
|---|---|---|---|
| 9,103,364 B2* | 8/2015 | Lin | ..................... F16B 25/0015 |
| 2009/0245972 A1* | 10/2009 | Lin | ....................... F16B 25/103 |
| | | | 411/411 |
| 2016/0367304 A1* | 12/2016 | Lindner | ............. A61B 17/7035 |
| 2018/0266467 A1* | 9/2018 | Lin | ..................... F16B 25/0015 |

FOREIGN PATENT DOCUMENTS

| | | |
|---|---|---|
| CN | 105451674 A | 3/2016 |
| CN | 205626071 U | 10/2016 |
| CN | 108523975 A | 9/2018 |
| EP | 1207312 A2 | 5/2002 |

OTHER PUBLICATIONS

IB; Written Opinion dated Jun. 25, 2019 in Application No. PCT/CN2019/082922.
CNIPA; Notification to Grant Patent Right dated Mar. 21, 2019 in CN Application No. 201820664990.2.

* cited by examiner

MEDICAL ANTI-LOOSENING SCREW BASED ON ORGANISM OSTEOGENESIS FUNCTION

CROSS-REFERENCE TO RELATED APPLICATIONS

This application is a national stage application of PCT/CN2019/082922, filed on Apr. 16, 2019. The PCT application, claims priority to and the benefit of, Chinese Patent Application No. 201820664990.2, filed on May 4, 2018, entitled "Medical Screw Based on Organism Osteogenesis Function." Both of which are incorporated herein by reference in their entirety for all purposes.

TECHNICAL FIELD

The present disclosure relates to the technical field of medical devices, and in particular to a medical anti-loosening screw based on an organism osteogenesis function.

BACKGROUND ART

The word "fracture" has been associated with us since recorded human history. The human bone has the function of "osteoclastogenesis-osteogenesis", and the fracture has a self-healing tendency. The process of natural healing of the fracture can be roughly divided into a hematoma organization stage (two weeks), a callus formation stage (one to two months), and a bone remodeling stage (two months to two years). Nowadays, the "open reduction and internal fixation operation" with the aid of an internal fixation material has been widely used in the fields of trauma orthopedics (comminuted or open or other severe fractures), spinal surgery (spondylolisthesis, scoliosis, tuberculosis, tumors, severe degenerative diseases, etc.), joint surgery (joint replacement, etc.), cranio-maxillofacial surgery (denture implantation, etc.), and veterinarians, among others. It effectively maintains the stability of the fractured bone and causes the fracture healing process to safely pass through the "callus formation stage" into the "bone remodeling stage", and can significantly reduce complications such as fracture nonunion and denture instability. In addition, the internal fixation material has completed its function upon the fractured bone has passed through the "callus formation stage", and it is generally necessary to remove the internal fixation material at a later stage to prevent hindrance of further remodeling of the fractured bone at the later stage due to its "stress shielding" effect.

As the internal fixation materials have been widely used in the medical fields, some patients still have some problems after the internal fixation operation, the most important of which is the loosening of the internal fixation materials (screws).

Information disclosed in the Background Art section is only intended to facilitate understanding of the overall background art of the present disclosure and the working mechanism of the present disclosure, and shall not be deemed as admitting or implying in any form that the information constitutes the prior art well known to those skilled in the art.

SUMMARY

An object of the present disclosure is to provide a medical anti-loosening screw based on an organism osteogenesis function, which can be used in the medical fields such as orthopedics (spine, four limbs, pelvis, joints, etc.), maxillofacial surgery, odontology, and veterinarians, and which can be effectively prevented from postoperative loosening after being implanted.

To achieve the above-mentioned object, the following technical solutions are proposed in the present disclosure.

The present disclosure provides a medical anti-loosening screw based on an organism osteogenesis function, comprising: a screw head and a screw rod connected to the screw head, wherein the screw rod comprises a main rod and a thread spirally wound around the main rod; and a cross section of the main rod is in a non-circular shape.

Optionally, the cross section of the main rod is in a shape of fat triangle or quadrangle or pentagon or hexagon or ellipse.

Optionally, when the cross section of the main rod is in a shape of ellipse, a ratio between major and minor semi-axes of the ellipse is smaller than $\sqrt{2}$, and a cross-sectional area of an outer circle of the thread is 1.49 to 3.61 times as large as a cross-sectional area of the main rod.

Optionally, when the cross section of the main rod is in a shape of fat triangle, a cross-sectional area of an outer circle of the thread is 1.49 to 3.61 times as large as a cross-sectional area of the main rod.

Optionally, the cross section of the main rod is in a shape of square, and a cross-sectional area of an outer circle of the thread is 1.59 to 3.61 times as large as a cross-sectional area of the main rod.

Optionally, the cross section of the main rod is in a shape of regular pentagon, and a cross-sectional area of an outer circle of the thread is 1.44 to 3.61 times as large as a cross-sectional area of the main rod.

Optionally, the cross section of the main rod is in a shape of regular hexagon, and a cross-sectional area of an outer circle of the thread is 1.49 to 3.61 times as large as a cross-sectional area of the main rod.

Optionally, a ratio between a radius of an outer circle of the thread and a radius of a circumscribed circle of the main rod is 1.2 to 1.9.

Optionally, a ratio between an outer diameter and a pitch of the thread is 1.5 to 5.5.

Optionally, the screw rod, at its end facing away from the screw head, is provided with a tapping groove.

Optionally, a cavity structure is provided inside the main rod; and alternatively, the main rod is solid inside.

Optionally, the screw head is in a circular shape, and a hexagonal groove or a cross groove or a slotted groove or a Torx groove or a Pozidriv groove is provided on the screw head;

alternatively, the screw head is in a dovetail shape.

Optionally, the circular screw head is provided with a locking thread.

Optionally, the dovetail-shaped screw head is a universal-type screw head.

The medical anti-loosening screw based on an organism osteogenesis function according to the present disclosure has the following advantageous effects:

The present disclosure provides a medical anti-loosening screw based on an organism osteogenesis function, comprising: a screw head and a screw rod connected to the screw head; wherein the screw rod comprises a main rod and a thread spirally wound around the main rod; and a cross section of the main rod is in a non-circular shape.

When the medical anti-loosening screw based on an organism osteogenesis function according to the present disclosure is used clinically, a bone tunnel is formed after the screw is implanted by tapping, and the thread cuts into the side wall of the bone tunnel to get a grip thereon; there is a gap between the main diameter of the screw and the bone tunnel, and the gap is filled with "bone residues" formed after tapping. Since the bone of a living body has an osteogenic function, the "bone residues" will form osseous callus and even normal new bone tissue like "hardening concrete" after the "callus formation stage" within about one to two months after the operation, to construct a hard non-cylindrical bone tunnel and adhere closely around the main diameter of the screw, such that the side surface of the main rod of the screw is significantly restrained and a relatively strong side thrust resistance is generated when the screw is untightened. This side thrust resistance is much greater than a friction between the surface of a traditional screw and the bone tunnel and has the effect of getting the screw stuck, therefore the loosening rate and the pullout rate can be significantly reduced, and a significant anti-loosening effect can be achieved. In addition, if it is necessary to remove the anti-loosening screw in the later stage of bone healing, the screw may be removed smoothly by only increasing the screw untightening torque.

The medical anti-loosening screw based on an organism osteogenesis function according to the present disclosure is applicable to the medical fields such as orthopedics (spine, four limbs, pelvis, joints, etc.), maxillofacial surgery, odontology, and veterinarians, and can be effectively prevented from postoperative loosening after being implanted.

BRIEF DESCRIPTION OF DRAWINGS

In order to more clearly illustrate technical solutions of specific embodiments of the present disclosure or of the prior art, drawings required for use in the description of the specific embodiments or the prior art will be described briefly below. It is obvious that the drawings in the following description are merely illustrative of some embodiments of the present disclosure. It will be understood by those of ordinary skill in the art that other drawings can also be obtained from these drawings without any inventive effort.

REFERENCE SIGNS

Figure 1:
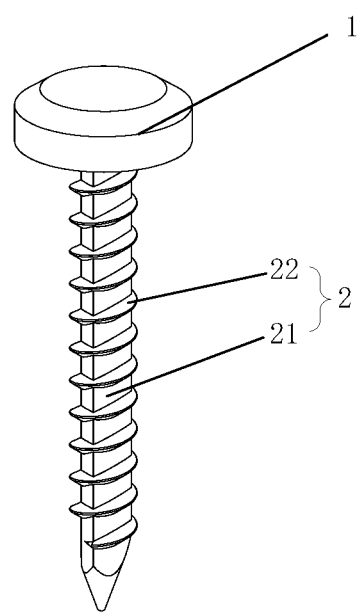
FIG. 1 is a schematic structural view of a medical anti-loosening screw based on an organism osteogenesis function according to an embodiment of the present disclosure.

1—screw head; 2—screw rod; 21—main rod; 22—thread.

DETAILED DESCRIPTION OF EMBODIMENTS

The technical solutions of the present disclosure will be described below clearly and completely with reference to the drawings. It is apparent that the embodiments to be described are some, but not all of the embodiments of the present disclosure. All the other embodiments obtained by those of ordinary skill in the art in light of the embodiments of the present disclosure without inventive efforts will fall within the scope of the present disclosure as claimed.

In the description of the present disclosure, it should be noted that orientation or positional relationships indicated by the terms such as "center", "up", "down", "left", "right", "vertical", "horizontal", "inside", and "outside" are the orientation or positional relationships shown based on the drawings, and these terms are intended only to facilitate the description of the present disclosure and simplify the description, but not intended to indicate or imply that the referred devices or elements must be in a particular orientation or constructed or operated in the particular orientation, and therefore should not be construed as limiting the present disclosure. In addition, the terms "first", "second", and "third" are used for descriptive purposes only, and should not be understood as an indication or implication of relative importance.

In the description of the present disclosure, it should be noted that the terms "mount", "couple", and "connect" should be understood broadly unless otherwise expressly specified or defined. For example, connection may be fixed connection or detachable connection or integral connection, may be mechanical connection or electric connection, or may be direct coupling or indirect coupling via an intermediate medium or internal communication between two elements. The specific meanings of the above-mentioned terms in the present disclosure can be understood by those of ordinary skill in the art according to specific situations.

The specific embodiments of the present disclosure will be described in detail below with reference to the drawings. It should be understood that the specific embodiments described herein are only intended to illustrate and explain the present disclosure, and are not intended to limit the present disclosure.

Referring to FIG. 1, FIG. 2, FIG. 3, FIG. 4, FIG. 5, and FIG. 6, a medical anti-loosening screw based on an organism osteogenesis function according to an embodiment of the present disclosure will be described in detail below with reference to the drawings.

An embodiment of the present disclosure provides a medical anti-loosening screw based on an organism osteogenesis function, comprising: a screw head 1 and a screw rod 2 connected to the screw head 1;

wherein the screw rod 2 comprises a main rod 21 and a thread 22 spirally wound around the main rod 21; and a cross section of the main rod 21 is in a non-circular shape.

When the medical anti-loosening screw based on an organism osteogenesis function according to an embodiment of the present disclosure is used clinically, a bone tunnel is formed after the screw is implanted by tapping, and the thread 22 cuts into the side wall of the bone tunnel to get a grip thereon; there is a gap between the main diameter of the screw and the bone tunnel, and the gap is filled with "bone residues" formed after tapping. Since the bone of a living body has an osteogenic function, the "bone residues" will form osseous callus and even normal new bone tissue like "hardening concrete" after the "callus formation stage" within about one to two months after the operation, to construct a hard non-cylindrical bone tunnel and adhere closely around the main diameter of the screw, such that the side surface of the main rod 21 of the screw is significantly restrained and a relatively strong side thrust resistance is generated when the screw is untightened. This side thrust resistance is much greater than a friction between the surface of a traditional screw and the bone tunnel and has the effect of getting the screw stuck, therefore the loosening rate and the pullout rate can be significantly reduced, and a significant anti-loosening effect can be achieved. In addition, if it is necessary to remove the anti-loosening screw in the later stage of bone healing, the screw may be removed smoothly by only increasing the screw untightening torque.

The medical anti-loosening screw based on an organism osteogenesis function according to the embodiment of the present disclosure is applicable to the medical fields such as orthopedics (spine, four limbs, pelvis, joints, etc.), maxillofacial surgery, odontology, and veterinarians, and can be effectively prevented from postoperative loosening after being implanted as compared with traditional medical anti-loosening screws.

In an optional solution of this embodiment, more optionally, the main rod 21 has a cross section in a shape of fat triangle or quadrangle or pentagon or hexagon or ellipse.

Figure 3:
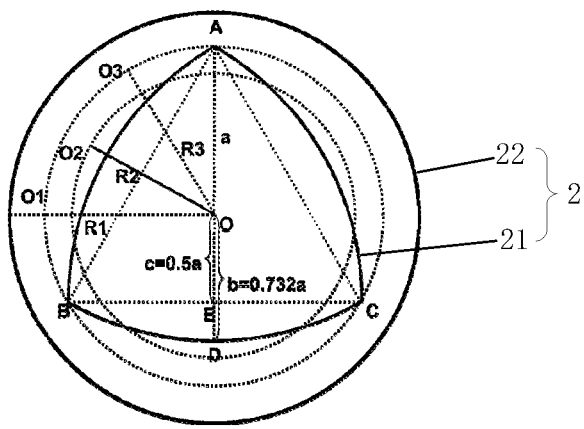
FIG. 3 is a schematic view of a main rod with a cross section in a shape of fat triangle according to an embodiment of the present disclosure.

In at least one embodiment, as shown in FIG. 1 and FIG. 3, the main rod 21 of the medical anti-loosening screw has a cross section in a shape of fat triangle. When the screw is used clinically, a bone tunnel is formed after the screw is implanted by tapping, and the thread 22 cuts into the side wall of the bone tunnel to get a grip thereon; there is a "crescent" gap between the main rod 21 of the screw and the bone tunnel, and the gap is filled with "bone residues" formed after tapping. Since the bone of a living body has an osteogenic function, the "bone residues" will form osseous callus and even normal new bone tissue like "hardening concrete" after the "callus formation stage" within about one to two months after the operation, to construct a hard bone tunnel being in a fat-triangular-prism shape and adhere closely around the main rod 21 of the screw, such that the side surface of the fat-triangular-prism-shaped main rod 21 of the screw is significantly restrained and a relatively strong side thrust resistance (which is similar to a driving force from a hexagonal socket screwdriver) is generated when the screw is untightened. This side thrust resistance is much greater than a friction between the surface of a traditional screw and the bone tunnel and has the effect of getting the screw stuck, therefore the loosening rate and the pullout rate can be significantly reduced, and a significant anti-loosening effect can be achieved. In addition, if it is necessary to remove the anti-loosening screw in the later stage of bone healing, the screw may be removed smoothly by only increasing the screw untightening torque. Screws in other shapes have similar action mechanisms.

It should be noted that the radius R2 of the main rod 21 of the traditional screw is set to be 1 (the radius R1 of the thread 22 is 1.5). Different cross-sectional shapes of the main rod 21 will be described in detail below.

Figure 2:
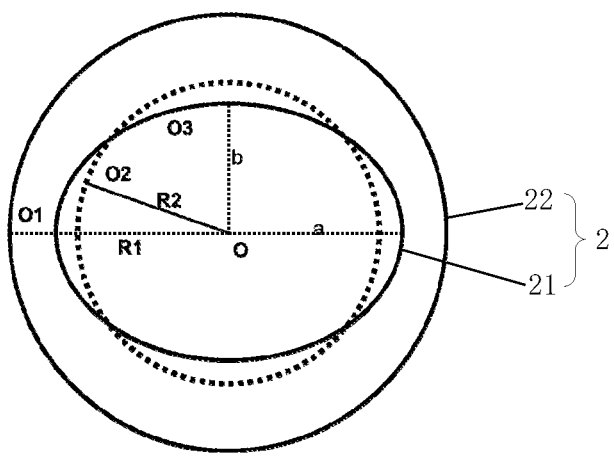
FIG. 2 is a schematic view of a main rod with a cross section in a shape of ellipse according an embodiment of the present disclosure.

When the main rod 21 has a cross section in a shape of ellipse, a ratio between major and minor semi-axes of the ellipse is smaller than $\sqrt{2}$, and the cross-sectional area of an outer circle of the thread 22 is 1.49 to 3.61 times, for example, but not limited to, 1.49, 1.69, 1.96, 2.25, 2.56, 2.89, 3.24, or 3.61 times, as large as the cross-sectional area of the main rod 21. As shown in FIG. 2, an imaginary concentric ellipse ⊙3 is drawn on the cross section, and major and minor semi-axes of the ellipse are defined as a and b in length, respectively, the radius is R3, $R1>a>R2=1>b$, and it is satisfied that $S\odot2=S\odot3$, and auxiliary lines are drawn as shown in FIG. 2. It can be obtained from $S\odot2=\pi\times R2\times R2=S\odot3=\pi\times a\times b$ that $a\times b=1$. It is suggested that $a=\sqrt{2}\times b$. It is calculated that the ellipse has a major semi-axis $a=1.19$ and a minor semi-axis $b=0.84$; the radius R1 of the outer circle of the thread 22 is in the range of (1.2 to 1.9), and for example, R1 may be, but is not limited to, 1.2, 1.3, 1.4, 1.5, 1.6, 1.7, 1.8, or 1.9. The cross-sectional area of the outer circle of the thread 22 is 1.49 to 3.61 times as large as the cross-sectional area of the main rod 21.

In an optional solution of this embodiment, more optionally, when the main rod 21 has a cross section in a shape of fat triangle, the cross-sectional area of the outer circle of the thread 22 is 1.49 to 3.61 times, for example, but not limited to, 1.49, 1.69, 1.96, 2.25, 2.56, 2.89, 3.24, or 3.61 times, as large as the cross-sectional area of the main rod 21. As shown in FIG. 3, an imaginary concentric circle ⊙3 with a radius of R3 is drawn on the cross section, where $R1\geq R3=a>R2=1$; A, B, and C are trisection points in the ⊙3, and arc BC, arc AC, and arc AB are drawn using line segments as a radius to each other, the "fat $\triangle ABC$" is defined as the boundary of the main rod 21 in a "fat triangular shape" and has a "constant height", and it is satisfied that $S\odot2=S\triangle ABC$; point D is taken as the midpoint of the arc BC, and standard auxiliary lines (dotted lines as shown in the figure) are drawn. Then, $AB=BC=AC=AD=\sqrt{3}a$, $b=(\sqrt{3}-1)a$, $c=\frac{1}{2}a$; and $AE=3/2a$. It is calculated that $R3=a=1.22$; the constant height AD of the cross section of the main rod 21 is 2.11; the radius R1 of the outer circle of the thread 22 is (1.22 to 1.9), and for example, R1 may be, but is not limited to, 1.22, 1.3, 1.4, 1.5, 1.6, 1.7, 1.8, or 1.9. The cross-sectional area of the outer circle of the thread 22 is 1.49 to 3.61 times as large as the cross-sectional area of the main rod 21.

Figure 4:
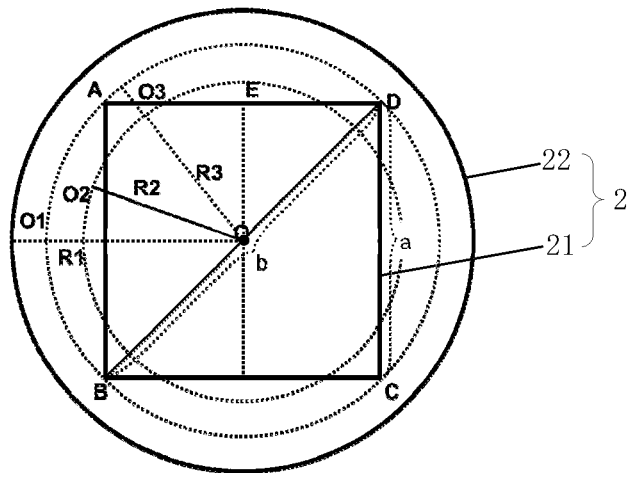
FIG. 4 is a schematic view of a main rod with a cross section in a shape of square according to an embodiment of the present disclosure.

In an optional solution of this embodiment, more optionally, the main rod 21 has a cross section in a shape of square, and the cross-sectional area of the outer circle of the thread 22 is 1.59 to 3.61 times, for example, but not limited to, 1.59, 1.69, 1.96, 2.25, 2.56, 2.89, 3.24, or 3.61 times, as large as the cross-sectional area of the main rod 21. As shown in FIG. 4, an imaginary concentric circle ⊙3 with a radius of R3 is drawn on the cross section, where $R1>R3>R2=1$; A, B, C, and D are the quarter points in the ⊙3, then □ABCD is a square and is defined as the boundary of the main rod 21 of the quadrangular screw, and auxiliary lines are drawn as shown in FIG. 4, where the side length is a, and the diagonal line has a length b, then $b=\sqrt{2}a$, and it is satisfied that $S\odot2=S\square ABCD$. It is calculated that the side length a of the main rod $21=\sqrt{\pi}\times R2=1.77$, and the diagonal line $b=\sqrt{2}\times a=\sqrt{2}\pi\times R2=2.51$; the radius R1 of the outer circle of the thread 22 is larger than $\frac{1}{2}\times b$, and thus R1 is in the range of (1.26 to 1.9), for example, R1 may be, but not limited to, 1.26, 1.3, 1.4, 1.5, 1.6, 1.7, 1.8, or 1.9. The cross-sectional area of the outer circle of the thread 22 is 1.59 to 3.61 times as large as the cross-sectional area of the main rod 21.

Figure 5:
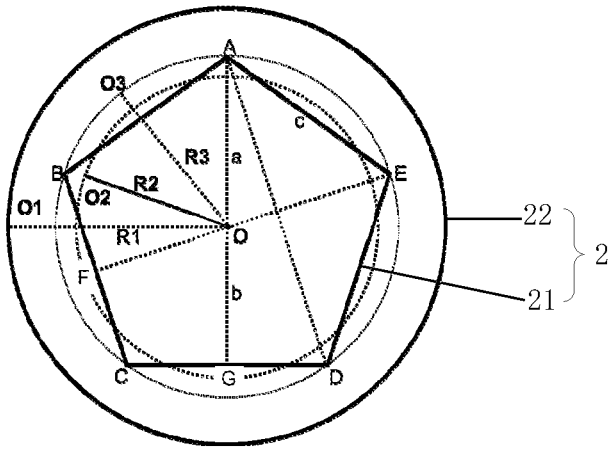
FIG. 5 is a schematic view of a main rod with a cross section in a shape of regular pentagon according to an embodiment of the present disclosure.

In an optional solution of this embodiment, more optionally, the main rod 21 has a cross section in a shape of regular pentagon, and the cross-sectional area of the outer circle of the thread 22 is 1.44 to 3.61 times, for example, but not limited to 1.44, 1.69, 1.96, 2.25, 2.56, 2.89, 3.24 or 3.61 times, as large as the cross-sectional area of the main rod 21. As shown in FIG. 5, an imaginary concentric circle ⊙3 with a radius of R3 is drawn on the cross section, where $R1>R3>R2=1$; A, B, C, D, and E are the quintile points in the ⊙3, then a pentagon ABCDE is a regular pentagon and is defined as the boundary of the main rod 21 of the pentagonal screw; and it is satisfied that $S\odot2=S$ pentagon ABCDE; auxiliary lines are drawn as shown in FIG. 5, where the side AE has a length c; the minimum diameter is the "height" $AG=a+b$; the maximum diameter is the "diagonal line" AD; the length of each side AB=BC=CD=DE=AE=c. Calculations related to the pentagon are carried out by the following methods:

Area $S_{pentagon\ ABCDE}=1.720 \times c \times c$;
Radius $R_3$ of the circumscribed circle=a=0.851×c;
Radius b of the inscribed circle=0.688×c;
Height AG=1.539×c;
Diagonal Line AD=1.618×c=1.902×a.
And $R_1>R_3>R_2=1$; it is satisfied that $S_{\odot 2}=S_{pentagon\ ABCDE}$, $S_{\odot 2}=\pi \times R_2 \times R_2 = S_{pentagon\ ABCDE}=1.720 \times c \times c$.

It is calculated that the radius a of the circumscribed circle=0.851×c=1.15; the side length c=1.35;

the minimum diameter, i.e., the "height" AG=1.539×c=2.08;

the maximum diameter, i.e., the "diagonal line" AD=1.618×c=2.19; and the radius $R_1$ of the outer circle of the thread 22 is in the range of (1.2 to 1.9), and for example, $R_1$ may be, but is not limited to, 1.2, 1.3, 1.4, 1.5, 1.6, 1.7, 1.8, or 1.9. The cross-sectional area of the outer circle of the thread 22 is 1.44 to 3.61 times as large as the cross-sectional area of the main rod 21.

Figure 6:
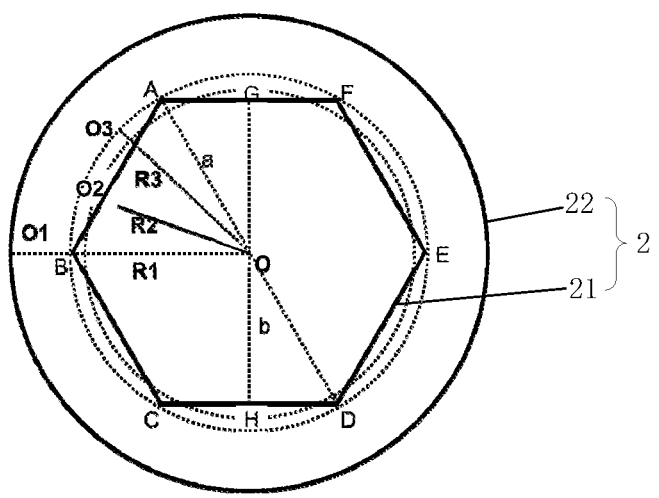
FIG. 6 is a schematic view of a main rod with a cross section in a shape of a regular hexagon according to an embodiment of the present disclosure.

In an optional solution of this embodiment, more optionally, the main rod 21 has a cross section in a shape of regular hexagon, and the cross-sectional area of the outer circle of the thread 22 is 1.49 to 3.61 times, for example, but not limited to, 1.49, 1.69, 1.96, 2.25, 2.56, 2.89, 3.24, or 3.61 times, as large as the cross-sectional area of the main rod 21. As shown in FIG. 6, an imaginary concentric circle ⊙3 with a radius of R3 is drawn on the cross section, where R1>R3>R2=1; A, B, C, D, E, and F are points for dividing the O3 into six equal parts, then a hexagon ABCDEF is a regular hexagon and is defined as the boundary of the main rod 21 of the hexagonal screw; and it is satisfied that S⊙2=S hexagon ABCDEF, and auxiliary lines are drawn as shown in FIG. 6; the length of each side and the radius of the circumscribed circle satisfy AB=BC=CD=DE=EF=OF=a=R3; the diagonal line AD=2a, and the height GH=2b=√2a.

It is calculated that the side length and the radius of the circumscribed circle satisfy AB=a=R3=1.10; the minimum diameter, i.e., the "height" GH=√3a=1.91; the maximum diameter, i.e., the "diagonal line" AD=2a=2.20; the radius R1 of the outer circle of the thread 22 is in the range of (1.2 to 1.9), and for example, R1 may be, but is not limited to, 1.2, 1.3, 1.4, 1.5, 1.6, 1.7, 1.8, or 1.9. The cross-sectional area of the outer circle of the thread 22 is 1.49 to 3.61 times as large as the cross-sectional area of the main rod 21.

In an optional solution of this embodiment, more optionally, the main rod 21 may have a cross section in a shape of non-circular shape other than fat triangle, square, regular pentagon, regular hexagon, or ellipse described above, and the ratio between the radius of the outer circle of the thread 22 and the radius of the circumscribed circle of the main rod 21 is 1.2 to 1.9, and may be for example, but not limited to, 1.2, 1.3, 1.4, 1.5, 1.6, 1.7, 1.8, or 1.9.

In an optional solution of this embodiment, more optionally, the ratio between the outer diameter and the pitch of the threads 22 is 1.5 to 5.5, and may be for example, but not limited to, 1.5, 2, 2.5, 3, 3.5, 4, 4.5, 5, or 5.5. A "tangent value" of an angle α between the thread 22 and the axis of the main rod 21 "multiplied by 2" (i.e., "the ratio of the outer diameter to the pitch" or "the number of complete threads 22 within a distance of an outer diameter") may be used as an index for the relative density and the gripping (or holding) force of the threads 22, the ratio is in the range of 1.5 to 5.5, and this ratio may be as low as 1 for a screw with double threads 22. When the ratio is larger, the angle α is larger, the threads 22 are more approximately perpendicular to the axis of the main rod 21 and are distributed at a higher density, and the screw has a greater pullout resistance.

In an optional solution of this embodiment, more optionally, the screw rod 2, at its end facing away from the screw head 1, is provided with a tapping groove. In at least one embodiment, the tip of the screw may be additionally designed as a self-tapping screw with a tapping groove.

In an optional solution of this embodiment, more optionally, a cavity structure is formed inside the main rod 21; alternatively, the main rod 21 is solid inside.

In an optional solution of this embodiment, more optionally, the screw head 1 is in a circular shape with or without a locking thread, and a hexagonal groove or a cross (or Phillips) groove or a slotted groove or a Torx groove or a Pozidriv groove is formed on the screw head 1;

alternatively, the screw head 1 is a universal-type screw head that is freely turnable, and the screw head is in a dovetail shape.

It should be noted that the screw head 1 may be designed in a circular shape with an internal hexagonal groove, a circular shape with a cross (or Phillips) groove, a circular shape with a slotted groove, a circular shape with an internal Torx groove, or a circular shape with a Pozidriv groove (trauma orthopedics, joint surgery, or cranio-maxillofacial surgery), or designed as a dovetail-shaped universal or fixed, or long dovetail-shaped pulling screw head 1 (spine surgery), or the like, according to the professional differences in its application fields.

Although the medical anti-loosening screw based on an organism osteogenesis function according to the present disclosure has been described above, the present disclosure is not limited to the above specific embodiments, and various variations or changes can be made without departing from the scope of the claims. The present disclosure includes various variations and changes made within the scope of the claims.

Finally, it should be noted that the above embodiments are merely intended to illustrate the technical solutions of the present disclosure, but not intended to limit the present disclosure. Although the present disclosure has been described in detail with reference to the foregoing embodiments, it should be understood by those of ordinary skill in the art that the technical solutions disclosed in the foregoing embodiments may still be modified, or some or all of the technical features thereof may be replaced with equivalents; and these modifications or replacements will not cause the essence of the corresponding technical solutions to depart from the scope of the technical solutions of the embodiments of the present disclosure.

What is claimed is:

1. A medical anti-loosening screw based on an organism osteogenesis function, comprising:
   a screw head and a screw rod connected to the screw head, wherein the screw rod comprises a main rod connected to the screw head and a circular thread spirally wound around the main rod;
   wherein a cross section of the main rod is in a non-circular shape, and
   wherein the main rod has, at least where it connects to the screw head, a cross section in a three-point shape with the points connected by convex sides, wherein each convex side is created by an arc and wherein each point is a sharp point created by an intersection of the arcs creating adjacent ones of the convex sides.

2. The medical anti-loosening screw based on an organism osteogenesis function according to claim 1, wherein a cross-sectional area of an outer circle of the thread is 1.49 to 3.61 times as large as a cross-sectional area of the main rod.

3. The medical anti-loosening screw based on an organism osteogenesis function according to claim 1, wherein a ratio between a radius of an outer circle of the thread and a radius of a circumscribed circle of the main rod is 1 to 1.56.

4. The medical anti-loosening screw based on an organism osteogenesis function according to claim 1, wherein a ratio between an outer diameter and a pitch of the thread is 1.5 to 5.5.

5. The medical anti-loosening screw based on an organism osteogenesis function according to claim 1, wherein the screw rod, at its end facing away from the screw head, is provided with a tapping groove.

6. The medical anti-loosening screw based on an organism osteogenesis function according to claim 1, wherein a cavity structure is formed inside the main rod; or
the main rod is solid inside.

7. The medical anti-loosening screw based on an organism osteogenesis function according to claim 1, wherein the screw head is a circular screw head, and a hexagonal groove, a cross groove, a slotted groove, a Torx groove or a Pozidriv groove is provided on the screw head; or
the screw head is a dovetail-shaped screw head.

8. The medical anti-loosening screw based on an organism osteogenesis function according to claim 7, wherein the circular screw head is provided with a locking thread.

9. The medical anti-loosening screw based on an organism osteogenesis function according to claim 7, wherein the dovetail-shaped screw head is a universal-type screw head.

\* \* \* \* \*

UNITED STATES PATENT AND TRADEMARK OFFICE
CERTIFICATE OF CORRECTION

| | |
|---|---|
| PATENT NO. | : 11,369,423 B2 |
| APPLICATION NO. | : 16/645412 |
| DATED | : June 28, 2022 |
| INVENTOR(S) | : Siwang Hu et al. |

It is certified that error appears in the above-identified patent and that said Letters Patent is hereby corrected as shown below:

On the Title Page

Item (73) Assignee: please delete "Siwang Hu, Shanghai (CN)" and insert therefore -- Siwang Hu, Zhejiang (CN) and Jianru Xiao, Shanghai (CN) --

Signed and Sealed this
Second Day of May, 2023

Katherine Kelly Vidal
*Director of the United States Patent and Trademark Office*